United States Patent [19]

Kozlowski, Jr.

[11] 4,178,797
[45] Dec. 18, 1979

[54] SHARPNESS TESTING MACHINE

[75] Inventor: George J. Kozlowski, Jr., Billerica, Mass.

[73] Assignee: Rudolph Beaver, Inc., Belmont, Mass.

[21] Appl. No.: 866,849

[22] Filed: Jan. 4, 1978

[51] Int. Cl.² .................................... G01M 13/00
[52] U.S. Cl. ......................................... 73/104
[58] Field of Search .................................. 73/104

[56] References Cited

U.S. PATENT DOCUMENTS

| 1,176,291 | 3/1916 | Herbert et al. | 73/104 X |
| 3,931,732 | 1/1976 | Heitlinger | 73/104 |

Primary Examiner—James J. Gill
Attorney, Agent, or Firm—Robert E. Ross

[57] ABSTRACT

A machine for testing the sharpness of knives, particularly surgical knives, in which means is provided for grasping a cylindrical rod of material such as rubber or plastic so that a free end protrudes from the grasping mechanism, and means is provided for rotating the rod. A knife blade to be tested is mounted in a pivoted fixture which carries a predetermined weight and can be positioned so that the cutting edge of the blade rests in the side of the protruding end of the cylindrical rod. When the rod is rotated, the blade cuts into the rod, and the sharpness of the blade is determined by the number of turns required to cut through the rod.

4 Claims, 5 Drawing Figures

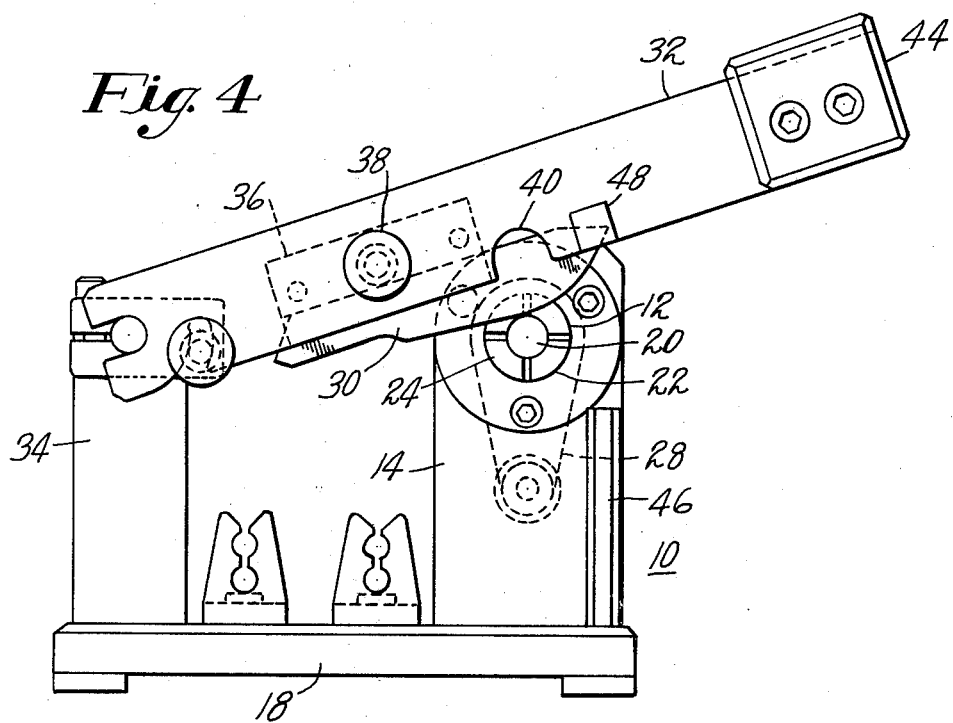
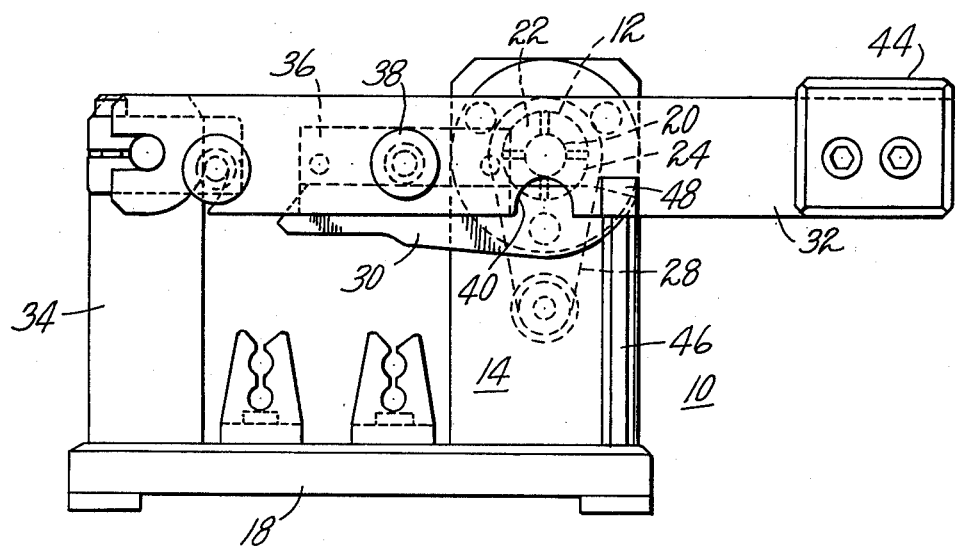

SHARPNESS TESTING MACHINE

BACKGROUND OF THE INVENTION

In the manufacture of surgical blades there has been needed a reliable, economical method of testing the sharpness of the blades produced, which gives consistent and reproducible results.

SUMMARY OF THE INVENTION

This invention provides a machine for testing the sharpness of surgical knives, in which a rotatable hollow mandrel, mounted in a suitable support, is provided with handle means at one end for rotating the mandrel and chuck means at the other end. A cylindrical rod of rubber or plastic is inserted into the mandrel with a free end protruding from the chuck, which grips the rod so that it is axially and rotationally fixed in relation to the mandrel.

A weighted arm is pivoted in a plane perpendicular to the axis of the mandrel and rod. The arm has means receiving a knife to be tested, in a position such that when the arm is lowered, the cutting edge of the knife rests on the upper surface of the protruding portion of the rod near the chuck.

When the mandrel is then rotated, the blade cuts into the rod more deeply with each turn. The number of turns required to completely sever the rod may then be used as a measure of the sharpness of the blade, with the sharper blades requiring fewer turns.

BRIEF DESCRIPTION OF THE DRAWING

FIG. 4 is a view of the machine of FIG. 2 as seen from the left end, at the start of a sharpness test.

FIG. 5 is a view similar to FIG. 5 at the completion of a sharpness test.

DESCRIPTION OF THE ILLUSTRATED EMBODIMENT

Figure 1:
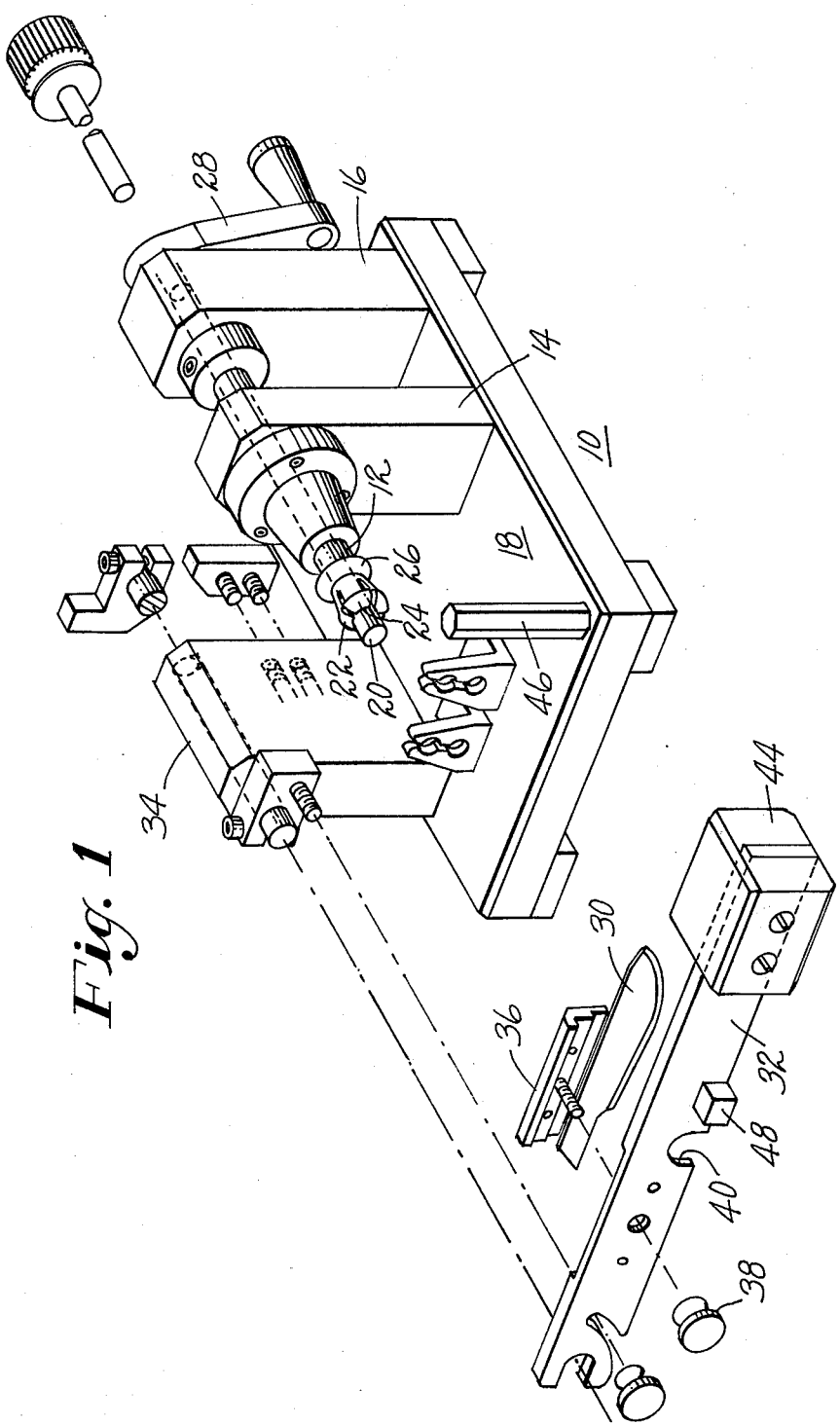
FIG. 1 is a partially exploded perspective view of a sharpness testing machine embodying the features of the invention, with the rod and knife blade in position for testing.
Figure 2:
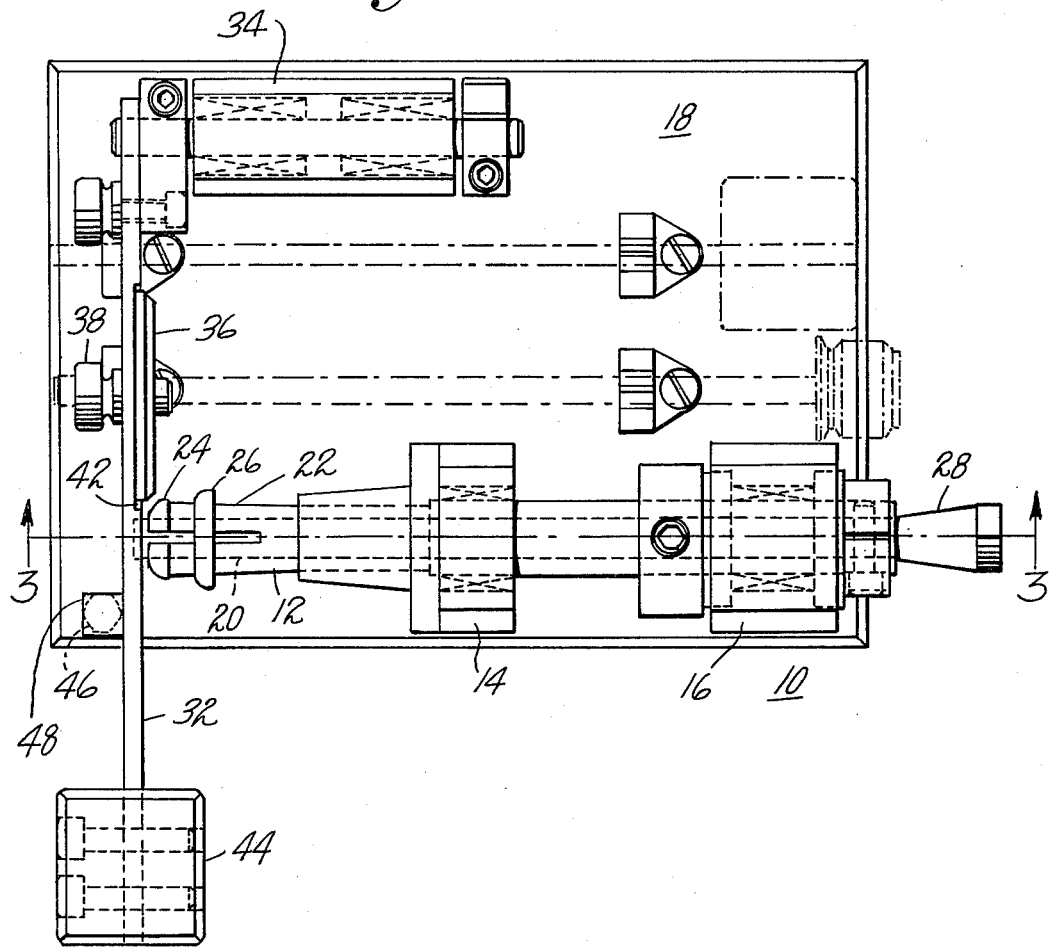
FIG. 2 is a top plan view of the machine of FIG. 1.
Figure 3:
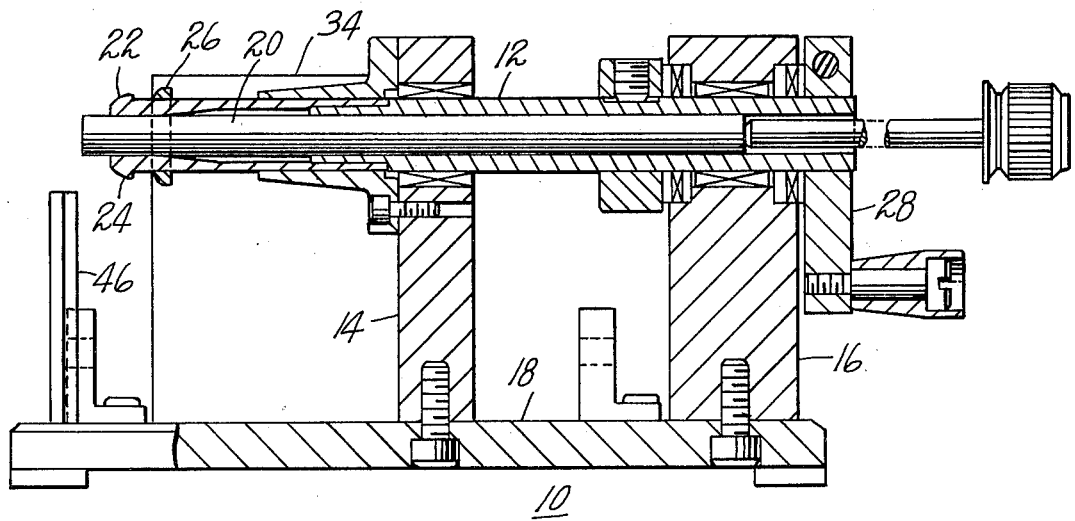
FIG. 3 is a view in section taken on line 3—3 of FIG. 2.

Referring to the drawing there is illustrated a machine 10, especially adapted for testing the sharpness of surgical blades.

The machine 10 comprises a hollow mandrel 12, rotatably mounted in a pair of supports 14 and 16 disposed on a base 18.

The mandrel 12 is intended to receive a rod 20, which may be formed of rubber or plastic of desired physical characteristics. To secure the rod in position, a chuck 22 is provided at the end, comprising resilient fingers 24 which may be flexed inwardly by a sliding ring 26 to grip the rod.

A crank 28 is provided at the other end to rotate the mandrel and rod for a purpose to appear hereinafter.

To retain and position a surgical blade 30 for testing, an arm 32 is mounted at one end into a support 34 for pivotal movement about said end in a plane perpendicular to the axis of the rod and mandrel. A clamp 36 and associated tightening screw 38 provide means for securing to the arm a blade 30 to be tested, in a position such that when the arm is lowered, the cutting edge of the blade rests on the rod 20 just in front of the chuck. A cut-out portion 40 is provided in the lower edge of the arm, positioned to be aligned with the rod 20 when the arm is lowered, to prevent interference between the arm and the rod during cutting. To position the forward end of the blade 30, a recess 42 is provided in the arm forwardly of the cut-out 40.

A weight 44 is mounted on the free end of the arm, and a stop 46 is provided in the base 18 positioned beneath an abutment 48 on the arm, to limit the downward movement of the arm after the rod has been cut through.

In operation, a rod of suitable material, such as rubber of known composition and physical characteristic is inserted into the mandrel so that an end protrudes from the chuck 22. The chuck is then tightened onto the rod by sliding the ring 26 forwardly so that the rod is clamped against axial movement, and so that it will rotate with the mandrel.

The blade 30 is then assembled onto the arm 32 by means of the clamp 36, and so positioned that a portion of the cutting edge extends across the cut-out portion 44 and the forward end of the blade rests in the recess 42.

The arm is then lowered so that the cutting edge rests on the rod with a predetermined force due to the weight 44. The crank 28 is then rotated slowly, at a constant rate, so that the rod rotates under the knife, and the knife cuts into the rod periphery.

The operator counts the number of turns of the handle, and when the knife has cut completely through the rod, the arm drops into the support, the number of turns made by the crank is recorded as a measure of the blade sharpness.

The sharpness rating determined by the above described test is comparative, that is, any test is merely a comparison with a blade of standard sharpness. For this purpose a safety razor blade may be used, since they are produced in large quantities with substantially uniform sharpness.

The rod may be of any suitable material, provided that the size, composition and physical characteristics are similar from one test to another. Buna rubber with a durometer hardness of 60 has been found satisfactory.

The machine is useful as a production quality control tool in the manufacture of surgical blades, and may also be used in hospitals as a blade testing device, and by salesmen as a demonstration tool.

Since changes apparent to one skilled in the art may be made in the illustrated embodiment of the device, without departing from the scope of the invention, it is intended that all matter contained herein be interpreted in an illustrative and not a limitative sense.

I claim:

1. A machine for testing the sharpness of knife blades comprising means for supporting an elongated cylindrical rod of test material so that an end portion thereof protrudes from the support means, an arm pivoted at one end and having a weight spaced from the pivot point, said arm carrying means for retaining a knife blade to be tested, said arm being pivoted in a plane perpendicular to the axis of the rod and so positioned that when the arm with a retained test blade is lowered toward the rod, the cutting edge of the blade rests on the periphery of the protruding end portion of the rod with a predetermined force, and means for rotating the rod so that the cutting edge of the blade cuts into the surface of the rod.

2. A machine for testing the sharpness of knife blades, comprising an elongated hollow mandrel mounted so as to be rotatable about its longitudinal axis, means at one end of the mandrel for gripping a rod of test material disposed in and extending from the mandrel to prevent axial movement of the rod in the mandrel and to cause the rod to rotate with the mandrel, means for rotating the mandrel, and a blade carrier pivotally mounted at one end and having a weight spaced from said one end, said arm having means for retaining a surgical blade, said means being so positioned on the blade carrier and the blade carrier being so positioned such that when the blade carrier is lowered with a blade assembled therewith, the cutting edge of the blade rests on the portion of the rod extending from the mandrel.

3. A machine as set out in claim 2 in which the blade carrier is pivoted in a plane perpendicular to the axis of the mandrel.

4. A method of testing the sharpness of a knife blade, comprising providing an elongated cylindrical rod of predetermined composition, resting a knife blade against the rod with the blade being perpendicular to the rod axis, forcing the blade against the rod with a predetermined force, and rotating said rod so that the blade cuts into the cylinder and continuing said rotation until the cylinder is cut completely through, whereby the number of rotations required to cut completely through the rod can be used as a measure of blade sharpness.

* * * * *